United States Patent

Keller et al.

[11] Patent Number: 5,869,099
[45] Date of Patent: Feb. 9, 1999

[54] COSMETIC COMPOSITION WITH POLYMER-BOUND BENZOPHENONE CHROMOPHORES

[75] Inventors: Harald Keller, Ludwigshafen; Karin Sperling-Vietmeier; Horst Westenfelder, both of Neustadt, all of Germany

[73] Assignee: BASF Aktiengesellschaft, Ludwigshafen, Germany

[21] Appl. No.: 917,340

[22] Filed: Aug. 26, 1997

[30] Foreign Application Priority Data

Aug. 26, 1996 [DE] Germany ............. 196 34 401.8

[51] Int. Cl.$^6$ ................................. A61K 7/42
[52] U.S. Cl. ................ 424/486; 424/487; 424/501; 424/59; 424/60; 424/78.18; 424/78.19; 424/78.2; 424/78.26; 424/78.27; 424/78.29; 424/78.33
[58] Field of Search ............. 424/486, 487, 424/501, 59, 60, 8.18, 78.19, 8.2, 78.26, 78.27, 78.29, 78.33

[56] References Cited

U.S. PATENT DOCUMENTS

| | | | |
|---|---|---|---|
| 3,341,493 | 9/1967 | Goldberg et al. | 260/47 |
| 3,956,244 | 5/1976 | Carpenter et al. | 526/79 |
| 4,524,061 | 6/1985 | Cho et al. | 424/60 |
| 5,041,282 | 8/1991 | Sabatelli et al. | 424/59 |

FOREIGN PATENT DOCUMENTS

| | | |
|---|---|---|
| 348 513 | 1/1990 | European Pat. Off. . |
| 60 88066 | 5/1985 | Japan . |

*Primary Examiner*—Nathan M. Nutter
*Attorney, Agent, or Firm*—Keil & Weinkauf

[57] ABSTRACT

A cosmetic composition comprises a polymer with the repeating structural unit (I)

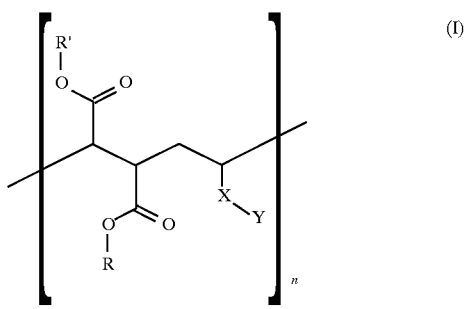

where
R and R' can be identical or different and are H, alkali metal, ammonium, $C_1$–$C_{30}$ alkyl,
X is a direct linkage, $C_1$–$C_8$ alkylene or $C_2$–$C_{12}$ oxoalkylene having 1–6 oxygen atoms,
Y is a UV-absorbing organic radical,
n is 2–800.

5 Claims, No Drawings

COSMETIC COMPOSITION WITH POLYMER-BOUND BENZOPHENONE CHROMOPHORES

The present invention relates to cosmetic compositions with polymer-bound chromophoric groups for protecting the skin and the hair from UV radiation.

Good resistance to water is often desirable for cosmetic sunscreen compositions which are applied to the skin. This property is particularly desired when the skin is frequently in contact with water or aqueous liquids such as perspiration. Polymers are often added to such compositions in order to achieve the required resistance to water.

Another possibility is to link the UV-absorbing groups covalently to a polymer.

WO 89/4824 describes copolymers of the UV-absorbing styrene and maleic anhydride, vinylpyrrolidone or acrylates. These copolymers have a high solubility in water and low penetration into the skin.

JP 60/88066 describes UV-absorbing benzophenone derivatives which are linked via a urethane spacer to (meth) acrylates. These polymers are suitable as material for contact lenses and spectacle lenses.

Besides good resistance to water, the cosmetic compositions should, however, comply with a number of other properties such as low penetration into the skin, low content of residual monomers which must be avoided for toxicological and olfactory reasons, good processability, miscibility and stability with other components of cosmetic compositions.

We have found cosmetic compositions comprising a polymer with the repeating structural unit (I)

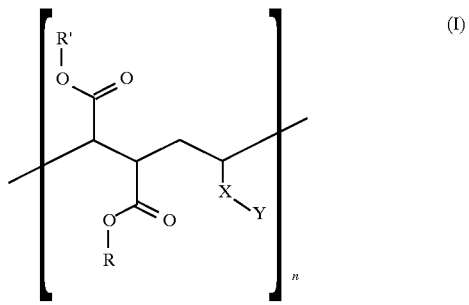

where
R and R' can be identical or different and are a, alkali metal, ammonium, $C_1$–$C_{30}$ alkyl,
X is a direct linkage, $C_1$–$C_8$ alkylene or $C_2$–$C_{12}$ oxoalkylene having 1–6 oxygen atoms,
Y is a UV-absorbing organic radical,
n is 2–800.

The solubility of polymers with the structural unit (X) can be adjusted as required by the nature of the radicals R and R'. If, for example, a polymer which is soluble in water or aqueous solvents is required, the radical R or R' is preferably hydrogen or alkali metal ions such as sodium and potassium or ammonium ions. The radical R does not have to be identical throughout the polymer but can also consist of mixtures of different radicals R and R'.

If, for example, the polymer with R=H is partially neutralized with the base NaOR, some of the radicals R are E and some are Na, depending on the degree of neutralization.

If, on the other hand, an oil-soluble polymer is required, as a rule R and R' are a long-chain hydrophobic radical. Preferred radicals R and R' for this purpose are long-chain branched or unbranched alkyl radicals having 12–30, particularly preferably 16–20, carbon atoms. However, it is also possible to use other radicals R and R', for example mono- or polyunsaturated hydrophobic alkenyl radicals.

The polymers for the cosmetic compositions according to the invention can be prepared by polymerizing monomers of the formula II under the conditions customary for free-radical polymerizations with exclusion of oxygen.

X is a direct linkage, $C_1$–$C_8$-alkylene or $C_2$–$C_{12}$-oxoalkylene having 1–6 oxygen atoms,
Y is a UV-absorbing organic radical.

Suitable solvents are the usual organic solvents, in particular esters such as ethyl acetate and butyl acetate, ketones such as acetone, methyl ethyl ketone and cyclohexanone, ethers such as tetrahydrofuran and methyl tert-butyl ether and alkanes such as hexane, heptane, cyclohexane and octane. Suitable initiators are azo initiators such as azoisobutyronitrile and peroxides such as dibenzoyl peroxide or tert-butyl 2-ethylperhexanoate. The reaction is carried out at from 40° to 160° C., preferably 80° to 120° C.

Monomers of the formula (II) can be prepared by the following known processes;

1-Olefin ethers
By Williamson synthesis from the corresponding 1-olefin chlorides or 1-olefin bromides and the UV-absorbing chromophores having OH groups (see J. March, Advanced Organic Chemistry, J. Wiley & Sons, 1985, page 342).

1-Olefin esters
By esterification of UV-absorbing chromophores with the corresponding 1-olefin alcohols (see J. March, Advanced Organic Chemistry, J. Wiley & Sons, 1985, page 348).

Vinyl esters
By transesterification of the corresponding carboxyl-containing UV-absorbing chromophores with vinyl acetate (see G. Heublein, B. Heublein, B. Heyroth, E. Brendel, Z. Chem. 19 (1979) 104).

Vinyl ethers
By reacting the UV-absorbing chromophores having OH groups with acetylene (see Organikum, Deutscher Verlag der Wissenschaften, Berlin, 1979, page 338).

Besides the monomers of the formula II, it is possible to include other vinylic comonomers such as vinylpyrrolidone, vinyl acetate, 1-olefins, acrylates and methacrylates in the polymer.

The polymer obtained in this way is subsequently reacted with R—OH and R'—OH. It is possible in this case to adjust the solubility properties of the polymer as required by the choice of the group R. If an aqueous base is chosen as R—OH a water-soluble polymer is obtained. If, on the other hand, the anhydride is reacted with a fatty alcohol, the polymer is oil-soluble.

The polymer obtained after reaction with R—OH is then formulated with ancillary substances and additives customary in cosmetics depending on the purpose of use Examples of suitable ancillary substances and additives for sunscreen compositions are described in W. Umbach, Kosmetik, Georg-Thieme-Verlag Stuttgart, 1988.

The cosmetic compositions according to the invention have good resistance to water, are very compatible with skin and show low penetration in to the skin.

The invention is further illustrated by the following examples.

EXAMPLE 1a
Preparation of a UV-absorbing polymer 3.85 g of maleic anhydride and 4 g of butyl acetate are heated to 100° C. under nitrogen. Over the course of 2 h, a solution of 7.5 g of vinyl p-dimethylaminobenzoate in 18 g of butyl acetate and 0.91 g of -t-butyl peroxy-2-ethylhexanoate in 10 g of butyl acetate are metered in from separate vessels. After addition of the two solutions is complete, the mixture is stirred at 100° C. for 4 h. After cooling, the reaction mixture is poured into 300 ml of t-butyl methyl ether, and the precipitated polymer is removed by filtration.

Yield: 2.17 g

GPC molecular weight: Mn=1370 g/mol, polydispersity=1.8

UV: 314 nm, $E^1_1$=624

EXAMPLE 1b
Preparation of an oil-soluble polymeric UV absorber 1.98 g of the polymer prepared in Example 1a are mixed with 3.91 g of 2-octyldodecanol and stirred at 150° C. for 6 h. This results in a clear viscous polymer containing 42% of unreacted 2-octyldodecanol.

GPC molecular weight: Mn=3360 g/mol, polydispersity=1.3

UV: 306 nm, $E^1_1$=142

EXAMPLE 2
Preparation of a UV-absorbing polymer 14.84 g of maleic anhydride and 15.1 g of butyl acetate are heated to 100° C. under nitrogen. Over the course of 2 h, 25 g of vinyl salicylate and 3.19 g of t-butylperoxy-2-ethylhexanoate in 10 g of butyl acetate are metered in from separate vessels. After addition of the two solutions is complete, the mixture is stirred at 100° C. for 4 h. After cooling, the reaction mixture is poured into 500 ml of t-butyl methyl ether, and the precipitated polymer is removed by filtration.

Yield: 29.6 g

GPC molecular weight: Mn=1600 g/mol, polydispersity=3.9

UV: 309 nm, $E^1_1$=131

EXAMPLE 3
Preparation of an oil-soluble polymeric UV absorber 15 g of the polymer prepared in Example 2 are mixed with 32.5 g of 2-octyldodecanol and stirred at 150° C. for 14 h. This results in a cloudy viscous polymer containing 22% of unreacted 2-octyldodecanol. Precipitation in 250 g of ethanol results in a polymeric solid.

Yield: 16.8 g

GPC molecular weight: n=10600 g/mol

Polydispersity=2.1

UV: 310 nm, $E^1_1$=50

EXAMPLE 4
Preparation of a UV-absorbing polymer 8.47 g of maleic anhydride and 19.76 g of toluene are heated to 100° C. under nitrogen. Over the course of 2 h, a solution of 25 g of allyl 2,2-diphenyl-1-cyanoacrylate in 42 g of toluene and 0.67 g of t-butylperoxy-2-ethylhexanoate in 16 g of toluene are metered in from separate vessels. After addition of the two solutions is complete, the mixture is stirred at 100° C. for 4 h. After cooling, the reaction mixture is poured into 500 ml of t-butyl methyl ether, and the precipitated polymer is removed by filtration.

Yield: 5.8 g

GPC molecular weight: mn=1620 g/mol, polydispersity=1.4

UV: 305 nm, $E^1_1$=252

EXAMPLE 5
Preparation of a UV-absorbing polymer 9.86 g of maleic anhydride and 50 g of tetrahydrofuran are heated to 75° C. under nitrogen. Over the course of 1 h, a solution of 25 g of vinyloxyethyl p-methoxycinnamate and 2.02 g of 1-dodecanethiol in 24 g of tetrahydrofuran and 0.34 g of 2,2-azobis(2-methyl-butyronitrile) in 10 g of tetrahydrofuran are metered in from separate vessels. After addition of the two solutions is complete, the mixture is stirred at 75° C. for 8 h. After cooling, the reaction mixture is poured into 300 ml of t-butyl methyl ether, and the precipitated polymer is removed by filtration.

Yield: 30 g

GPC molecular weight: Mn=2800 g/mol, polydispersity=2.8

UV: 310 nm, $E^1_1$=292

EXAMPLE 6
Preparation of a UV-absorbing polymer 57.8 g of maleic anhydride and 58 g of butyl acetate are heated to 100° C. under nitrogen. Over the course of 4 h, a solution of 150 g of 2-hydroxy-4-allyloxybenzophenone in 280 g of butyl acetate and 16.6 g of t-butyl peroxy-2-ethylhexanoate in 10 g of butyl acetate are metered in from separate vessels. After addition of the two solutions is complete, the mixture is stirred at 100° C. for 2 h. After cooling, the reaction mixture is poured into 5 l of t-butyl methyl ether, and the precipitated polymer is removed by filtration.

Yield: 196.8 g

GPC molecular weight: Mn=1744 g/mol, polydispersity=1.7

EXAMPLE 7
Preparation of an oil-soluble polymeric UV absorber 100 g of the polymer prepared in Example 6 are mixed with 170 g of 2-octyldodecanol and stirred at 150° C. for 5 h. This results in a clear viscous polymer containing 16.5% of unreacted 2-octyldodecanol.

GPC molecular weight: Mn=5510 g/mol, polydispersity=1.8

UV: 314 nm, $E^1_1$=92

274 nm, $E^1_1$=147

EXAMPLE 8
Preparation of a water-soluble polymeric UV absorber 10 g of the polymer prepared in Example 6 are suspended in 100 g of water. Then 1.14 g of sodium hydroxide are added and the mixture is heated at 100° C. for 10 min to result in a clear yellow solution. The aqueous polymer solution can be further diluted with water.

EXAMPLE 9

The polymer solution prepared in Example 8 is acidified to pH 2 by adding 32 percent strength hydrochloric acid. A colorless polymer precipitates.

Yield: 9 g

EXAMPLE 10
Preparation of a sunscreen composition

Phase A; 18 g of the polymer prepared in Example 7, 5 g of Finsolv TN, 10 g of Witconol APM and 0.5 g of Nip Nip are mixed at 60° C. and, after cooling, mixed with 1 g of Cremophor RH40.

Phase C: 0.3 g of Pemulen TRI, 5 g of 1,2-propylene glycol and 65 g of water are mixed and then 0.2 g of Tylose H4000 is stirred in.

Phase A is stirred into phase C and neutralized by adding 0.3 g of triethanolamine.

We claim:

1. A cosmetic composition comprising a polymer with the repeating structural unit (I)

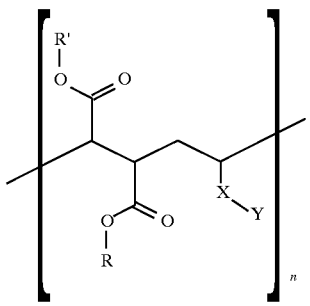

where

R and R' can be identical or different and are H, alkali metal, ammonium or $C_1$–$C_{30}$ alkyl, X is a direct linkage, $C_1$–$C_8$ alkylene or $C_2$–$C_{12}$ oxoalkylene having 1–6 oxygen atoms, Y is a UV-absorbing organic radical, n is 2–800.

2. A cosmetic composition as defined in claim 1, wherein R and R' are branched or unbranched alkyl radicals having 8–20 carbon atoms.

3. A cosmetic composition as defined in claim 1, wherein Y absorbs light of the wavelength 200–400 nm.

4. A cosmetic composition as claimed in claim 1, wherein Y is selected from the group consisting of

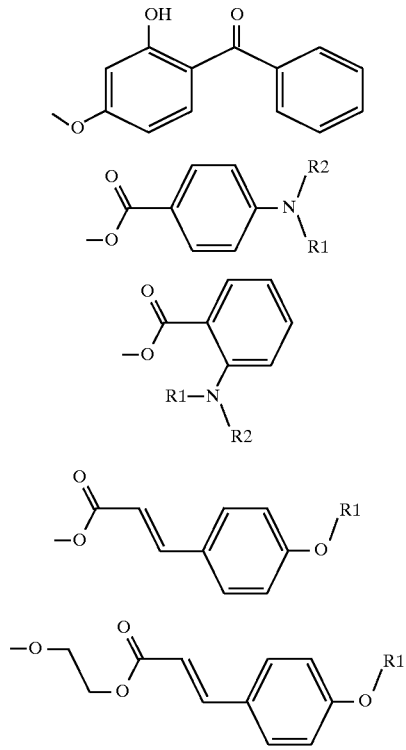

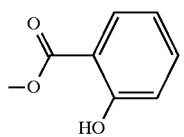

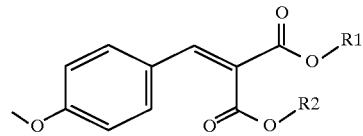

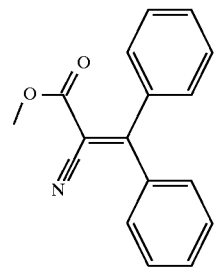

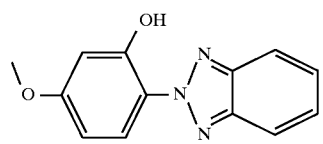

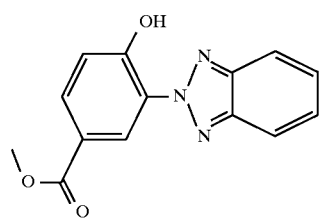

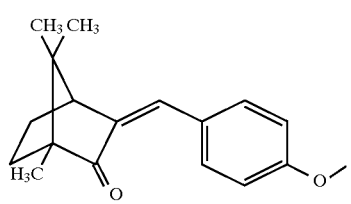

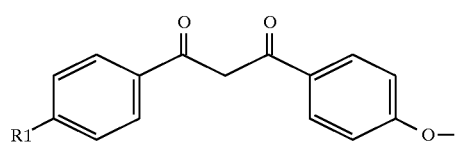

and $R^1$ and $R^2$ are identical or different, and are H, $C_1$–$C_6$-alkyl or $C_2$–$C_{12}$ oxoalkyl having 1–6 oxygen atoms.

5. A process for producing a cosmetic composition containing a polymer with the repeating structural unit (I)

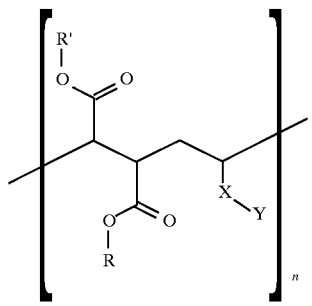

where
R and R' can be identical or different and are H, alkali metal, ammonium or $C_1$–$C_{30}$-alkyl,
X is a direct linkage, $C_1$–$C_8$-alkylene or $C_2$–$C_{12}$-oxoalkylene having 1–6 oxygen atoms,
Y is a UV-absorbing organic radical, n is 2–800 which comprises a) polymerizing maleic anhydride with a monomer of the formula II

where X and Y have the meanings indicated above, b) reacting the resulting polymer with R—OH and R'—OH where R and R' have the meanings indicated above and c) formulating the polymer obtained in b) with conventional ancillary substances and carriers.

* * * * *